United States Patent [19]

Miyashita et al.

[11] 4,256,746
[45] Mar. 17, 1981

[54] DECHLOROMAYTANSINOIDS, THEIR PHARMACEUTICAL COMPOSITIONS AND METHOD OF USE

[75] Inventors: Osamu Miyashita, Osaka; Hiroshi Akimoto, Nishinomiya, both of Japan

[73] Assignee: Takeda Chemical Industries, Osaka, Japan

[21] Appl. No.: 92,954

[22] Filed: Nov. 9, 1979

[30] Foreign Application Priority Data

Nov. 14, 1978 [JP] Japan .................................. 53-13995
Jun. 11, 1979 [JP] Japan .................................. 54-73790

[51] Int. Cl.³ .................. C07D 498/06; A61K 31/535
[52] U.S. Cl. ...................... 424/248.54; 260/239.3 P
[58] Field of Search ........................... 260/239.3 P; 424/248.54

[56] References Cited

U.S. PATENT DOCUMENTS

| | | | |
|---|---|---|---|
| 3,896,111 | 7/1975 | Kupchan et al. | 260/239.3 P |
| 4,137,230 | 1/1979 | Hashimoto et al. | 260/239.3 P |
| 4,162,940 | 7/1979 | Higashide et al. | 435/119 |

OTHER PUBLICATIONS

Kupchan et al., "J. Med. Chem.", (1978), vol. 21, No. 1, pp. 31-37.
March, "Advanced Organic Chemistry", (McGraw-Hill), pp. 439-440 (1968).

*Primary Examiner*—Henry R. Jiles
*Assistant Examiner*—Robert T. Bond
*Attorney, Agent, or Firm*—Wegner & Bretschneider

[57] ABSTRACT

Novel dechloromaytansinoids of the formula:

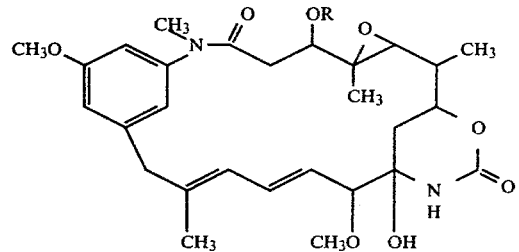

wherein R is H or acyl having 1 to 20 carbon atoms, have antimitotic, antitumor and antimicrobial activities.

15 Claims, No Drawings

DECHLOROMAYTANSINOIDS, THEIR PHARMACEUTICAL COMPOSITIONS AND METHOD OF USE

This invention relates to dechloromaytansinoid compounds of the formula:

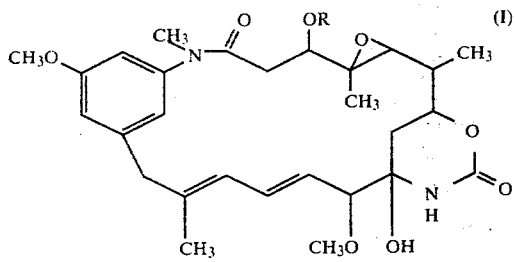

wherein R is H or acyl having 1 to 20 carbon atoms, and to methods for production and use of the compounds (I).

Referring to the above formula (I), the acyl group R is an acyl group derived from a carboxylic acid having a molecular weight of up to about 300. The acyl group thus includes, among others, saturated or unsaturated aliphatic acyl groups, saturated or unsaturated alicyclic aryl groups, aromatic acyl groups, saturated or unsaturated heterocyclic acyl groups and N-acyl-α-amino acid acyl groups. These acyl groups may be represented by the following formula:

wherein $R^2$ is H, alkyl, alkenyl, cycloalkyl, cycloalkenyl, aryl or heterocyclic group, any of which may optionally be substituted, the cyclic groups being attached, directly or through an alkylene chain, to the carboxyl group in the formula (A). Among these groups, those having substituents may for instance be N-acyl-α-aminoacyl groups of the following formula:

wherein $R^3$ is H, alkyl, cycloalkyl, aryl, indolyl or imidazolyl, any of which groups may optionally be substituted, the cyclic groups being attached to the α-carbon atom directly or through an alkylene chain; $R^4$ is H, alkyl, cycloalkyl or aryl, any of which groups may optionally be substituted, the cyclic groups being attached to the N-atom directly or through an alkylene chain; $R^5$ is H, alkyl, alkenyl, cycloalkyl, cycloalkenyl, aryl or heterocyclic group, any of which groups may optionally be substituted, the cyclic groups being attached to the carbonyl group on the N-atom directly or through the intermediary of an alkylene chain; and $R^5$ may further be alkoxy, bornyloxy, isobornyloxy or benzyloxy.

$R^2$ in the acyl group designated by the above formula (A) will now be described in detail.

The alkyl group $R^2$ includes, among others, alkyls of about 1 to 18 carbon atoms (e.g. methyl, ethyl, propyl, isopropyl, butyl, isobutyl, sec-butyl, tert-butyl, pentyl, isopentyl, 1-methylpropyl, hexyl, heptyl, 3-heptyl, octyl, nonyl, decyl, undecyl, dodecyl, tridecyl, pentadecyl, heptadecyl) and, preferably, represents an alkyl group of about 1 to 6 carbon atoms.

The alkenyl group $R^2$ includes, among others, alkenyls of about 2 to 10 carbon atoms (e.g. vinyl, allyl, 1-methyl-vinyl, 2-methyl-vinyl, 1-octenyl, 1-decenyl) and, preferably, represents an alkenyl group of about 2 to 4 carbon atoms.

The cycloalkyl group $R^2$ includes, for example, cycloalkyls of about 3 to 10 carbon atoms (e.g. cyclopropyl, cyclobutyl, cyclopentyl, cyclohexyl, cycloheptyl, cyclooctyl, norbornyl, adamantyl) and, preferably, represents a cycloalkyl group of 3 to 7 carbon atoms.

The cycloalkenyl group $R^2$ includes, for example, cycloalkenyls of about 3 to 10 carbon atoms (e.g. 1-cyclobutenyl, 1-, 2- or 3-cyclopentenyl, 1-, 2- or 3-cyclohexenyl, 4-cycloheptenyl, 4-cyclooctenyl, 1, 4-cyclohexadienyl, 4-norbornenyl, 2,4,6-cycloheptatrienyl.)

The aryl group $R^2$ may for example be phenyl or naphthyl, and preferably is phenyl.

The heterocyclic group $R^2$ includes saturated or unsaturated 4-, 5- or 6-membered heterocyclic groups including N, O or/and S atoms, to which groups a benzene ring may optionally be fused. Thus, the N-containing 4-, 5- or 6-membered heterocyclic groups include, for example, azetidinyl, pyridyl, 1,2,3,4-tetrahydropyridyl, piperidyl, quinolyl, 1,2-dihydroquinolyl, 3- or 4-isoquinolyl, 1,2-dihydroisoquinolyl, pyrrolyl, pyrrolinyl, pyrrolidinyl, indolyl, etc. The O-containing 5- or 6-membered heterocyclic groups include furyl, pyranyl, dihydropyranyl, benzofuryl, benzopyranyl, etc. Among said S-containing 5- or 6-membered heterocyclic groups are thienyl, benzothienyl and so forth. Said heterocyclic group may includes 2 to 4 similar or dissimilar hetero-atoms such N, O or/and S. Thus, there may be mentioned, among others, imidazolyl, pyrazolyl, pyrazinyl, pirimidyl, piridazinyl, 2-imidazolinyl, imidazolidinyl, benzimidazolyl, indazolyl, quinoxalyl, quinazolinyl, cinnolinyl, 1,4-dioxanyl, 1,4-benzodioxanyl, 1,2- or 1,3-dithiolanyl, 1,3-dithianyl, isoxazolyl, oxazolyl, morpholinyl, benzisoxazolyl, benzoxazolyl, isothiazolyl, thiazolyl, benzisothiazolyl benzothiazolyl, benzothiazinyl, 1,2,4-, 1,2,5- or 1,3,4-oxadiazolyl, 1,2,3-, 1,2,4-, 1,2,5- or 1,3,4-thiadiazolyl, 1,2,3-, 1,2,5- or 1,3,4-triazolyl, 1,3,5-triazinyl, benzotriazolyl, 1,2,3,4-tetrazolyl, etc. Among these heterocyclic groups, those containing NH group, such as azetidinyl, 1,2,3,4-tetrahydropyridyl, piperidyl, 1,2-dihydroquinolyl, 1,2-dihydroisoquinolyl, pyrrolyl, pyrrolinyl, pyrrolidinyl, pyrazolyl, 2-imidazolinyl, imidazolidinyl, indazolyl, morpholinyl, 1,2,3-, 1,2,5- or 1,3,4-triazolyl, benzotriazolyl or 1,2,3,4-tetrazolyl, generally preferably have suitable substituents, such as those mentioned hereinafter, in the N-position or have an alkylene chain attached to the N-position.

The alkyl, alkenyl, cycloalkyl, cycloalkenyl, aryl and heterocyclic group, each represented by $R^2$, may optionally be substituted. The substituents may be such groups as, for example, alkoxy groups of 1 to 4 carbon atoms (e.g. methoxy, ethoxy, propoxy, isopropoxy, n-butoxy, isobutoxy, sec-butoxy, tert-butoxy), alkanoyl groups of 2 to 4 carbon atoms (e.g. acetyl, propionyl, n-butyryl, isobutyryl), alkanoyloxy groups of 2 to 4 carbon atoms (e.g. acetyloxy, propionyloxy, n-butyryloxy, isobutylyloxy), alkoxycarbonyl groups of 2 to 4 carbon atoms (e.g. methoxycarbonyl, ethoxycarbonyl, n-propoxycarbonyl, isopropoxycarbonyl), halogens (e.g. chlorine, fluorine, bromine, iodine), nitro, cyano, trifluoromethyl, di-$C_{1-4}$ alkylamino groups (e.g. dimethylamino, diethylamino, dipropylamino, diisopropylamino, dibutylamino), $C_{1-4}$ alkylthio groups (e.g. methylthio, ethylthio, n-propylthio, isopropylthio, n-butylthio, isobutylthio, sec-butylthio, tert-butylthio), methylsulfinyl, methylsulfonyl, oxo, thioxo, $C_{1-4}$ alkanoylamino groups (e.g. formamido, acetamido, propionylamido, butyrylamido, isobutyrylamido) and so forth. When $R^2$ is a cyclic group (cycloalkyl, cycloalkenyl, aryl or heterocyclic group), there may be present such substituents as alkyls of 1 to 4 carbon atoms (e.g. methyl, ethyl, n-propyl, iso-propyl, n-butyl, iso-butyl, sec-butyl, tert-butyl). One to 3 of such substituents may be present, and may be the same or different.

The cyclic group $R^2$ (the cycloalkyl, cycloalkenyl, aryl or heterocyclic group which may optionally be substituted) may be combined to the carbonyl group in the formula —$COR^2$ through an alkylene chain. The alkylene chain may for example be a straight-chain or branched alkylene group of about 1 to 4 carbon atoms [e.g. methylene, ethylene, methylmethylene (ethylidene), propylene, butylene, 1-, 2- or 3-methylpropylene, 1- or 2-ethylethylene, propylmethylene, 1,1- or 1,2-dimethylethylene, isopropylmethylene]. Such alkylene chain may also have substituents similar to those mentioned above. Therefore, when said cyclic group is attached to the alkylene chain, $R^2$ represents a cyclo alkylalkyl, cycloalkenylalkyl, aralkyl or heterocycle-alkyl group.

As examples of the substituted $C_{1-18}$ alkyls as designated by $R^2$, there may be mentioned methoxymethyl, butoxymethyl, methylthiomethyl, methylthioethyl, ethylthioethyl, isopropylthioethyl, butylthioethyl, isobutylthioethyl, acetyloxymethyl, acetyloxyethyl, ethoxycarbonylmethyl, butoxycarbonylethyl, fluoromethyl, chloromethyl, chloroethyl, 3-chloropropyl, 4-chlorobutyl, 3,3,3-trichloropropyl, trifluoromethyl, bromomethyl, 4-bromobutyl, 5-bromopentyl, iodomethyl, 2-iodoethyl, 1,1-dimethyl-2, 2-dichloroethyl, 2-chloro-1-chloromethyl-1-methylethyl, cyanomethyl, methylsulfinylethyl, methylsulfonylmethyl, etc.

The substituted alkenyl group of 2 to 10 carbon atoms, designated by $R^2$, may for example be 2-chlorovinyl.

The substituted $C_{3-10}$ cycloalkyl group $R^2$ includes, among others, 2,2-dimethylcyclopropyl, 2-propylcyclopropyl, 2-butylcyclopropyl, 4-isobutylcyclohexyl, 2-bromocyclopropyl, 2-chlorocyclobutyl, 4-chlorocyclohexyl, 2-iodocyclohexyl, 2,2-difluorocyclobutyl, 3-methoxycyclohexyl, 2,2-dimethyl-3-acetylcyclobutyl, 4-acetylcyclohexyl, 2-cyanocyclohexyl, 2-cyanocyclobutyl, 4-cyanocyclohexyl, 4-dimethylaminocyclohexyl, etc.

The substituted $C_{3-10}$ cycloalkenyl group $R^2$ includes, among others 2-cyano-2-cyclohexenyl, 3,3-dimethyl-4-cyclobutenyl, 4-ethoxycarbonyl-1-cyclohexenyl, 4-butoxycarbonyl-1-cyclohexenyl, etc.

The substituted aryl group $R^2$ includes, among others, 2-, 3- or 4-methylphenyl, 4-tert-butylphenyl, 2-, 3- or 4-chlorophenyl, 2-, 3- or 4 bromophenyl, 2-, 3- or 4-iodophenyl, 2-, 3- or 4-fluorophenyl, 2- or 4-methoxyphenyl, 4-butoxyphenyl, 4-methoxycarbonylphenyl, 3-acetylphenyl, 2-, 3- or 4-nitrophenyl, 3- or 4-cyanophenyl, 4-dimethylaminophenyl, 4-diethylaminophenyl, 4-acetoxyphenyl, 4-butyryloxyphenyl, 2,4-, 2,5-, 2,6-, 3,4- or 3,5-dichlorophenyl, 3,4-dimethoxyphenyl, 3,4,5-trimethoxyphenyl, 3,4-methylenedioxyphenyl, 3-trifluoromethylphenyl, 4-methylthiophenyl, 4-methylsulfonylphenyl, 4-acetamidophenyl, etc.

As examples of the substituted or unsubstituted 4-, 5 or 6-membered heterocyclic group $R^2$, there may be mentioned 1-acetyl-2-azetidinyl, 1-methyl-2-pyrrolyl 3-methoxy-2-furyl, 3-methyl-2-furyl, 5-methyl-2-furyl 5-nitro-2-furyl, 3-methyl-2-thienyl, 3-bromo-4,5-dimethyl-2-thienyl, 2-methyl-4-thiazolyl, 1,2-dimethyl-4-chloro-5-imidazolyl, 1-butyl-4-pyrazolyl, 2,4-dichloro-4-isothiazolyl, 5-methyl-1,2,3-thiadiazol-4-yl, 3,5-dimethyl-4-isoxazolyl, 2-methyl-5-diisopropylamino-4-oxazolyl, 5-methyl-1,2,5-oxadiazol-3-yl, 4-methoxy-1,2,5-oxadiazol-3-yl, 5-methyl-1,3,4-oxadiazol-2-yl, 3-methyl-1,2,3-thiadiazolyl-5-yl, 5-methyl-1,3,4-thiadiazol-2-yl, 5-methyl-1,2,3-thiadiazol-4-yl, 1-methyl-1,2,3-triazol-4-yl, 2-ethyl-1,2,3,4-tetrazol-5-yl, 5-nitro-2-pyridyl, 6-ethyl-4-pyridyl, 5-ethoxycarbonyl-3-pyridyl, 5-chloro-3-pyridyl, 1-butyryl-2-piperidyl, 2-oxo-5-pyranyl, 7-methoxy-3,4-dihydro-2H-2-pyranyl, 1-acetyl-2-pyrrolidinyl, 1-propyl-5-oxo-3-pyrrolidinyl, 3-methyl-2,4-dioxo-5-thiazolidinyl, 4-, 5-, 6- or 7-nitro-3-indolyl, 5-fluoro-2-indolyl, 2-methyl-5-methoxy-3-indolyl, 1-methyl-2-indolyl, 5-chloro-2-benzothienyl, 3-methyl-2-benzofuryl, 1-methyl-2-benzoimidazolyl, 6-nitro-2-benzothiazolyl, 4-chloro-3-quinolyl, 6-methoxy-2-quinolyl, 2,4-dimethoxy-3-quinolyl, 2-methyl-1-oxo-3-isocarbostyryl, 7-methyl-3-coumaryl, 4-methylquinazolyl, 3-propyl-2,4-dioxo-5-imidazolinyl, 7-methoxycarbonyl-2-oxo-1, 2-dihydro-3-quinazolyl, 2-furyl, 2-thienyl, 3-isoxazolyl, 4-imidazolyl, 1,2,5-thiadiazol-3-yl, 2-, 3- or 4-pyridyl, 2-pyradinyl, 2-pyrimidinyl, 2-s-triazinyl, 1,2-dithioranyl, 3-indolyl, 2-benzothienyl, 2-benzofuryl, 3-benzopyrazolyl, 2-benzimidazolyl, 2-benzoxazolyl, 3-benzisoxazolyl, 3-benzisothiazolyl, 2-benzothiazolyl, 2-benzo-1,4-oxazinyl, 3-quinolyl, 1-isoquinolyl, etc.

When the cyclic group $R^2$ [e.g. cycloalkyl, aryl (especially phenyl) or heterocyclic group] is combined to the carbonyl carbon of acyl group (A) through an alkylene chain, $R^2$ represents a combination of such a cyclic group and an alkylene group, thus meaning cycloalkylalkyl, cycloalkenylalkyl, aralkyl or heterocycle-alkyl. Such cycloalkylalkyl and cycloalkenylalkyl groups include, for example, adamantyl methyl, cyclohexylmethyl, 3-cyclohexylpropyl, 2-cyclopentenylmethyl, 2-cyclopentenylethyl, etc. The aralkyl group includes, for example, 4-bromobenzyl, 2-, 3- or 4-chlorobenzyl, 2,5 or 3,4-dimethoxybenzyl, 4-ethoxybenzyl, 4-fluorobenzyl, 3- or 4-methoxybenzyl, 4-methoxyphenylethyl, 1- or 2-naphtylmethyl, 2-, 3- or 4-nitrobenzyl, 3-nitrophenethyl, benzyl, 2-, 3- or 4-phenylpropyl, 2-, 3- or 4-methylbenzyl, 3,4,5-trimethoxybenzyl, α-methylphenethyl, etc. The heterocycle-alkyl group includes, for example, 5-ethyl-3-indolylmethyl, 5-fluoro-3-indolylmethyl, 3-indolylmethyl, 3-indolyl-3-propyl, 5-methoxy-3-indolylmethyl, 5-methyl-3-indolylmethyl, 2-, 3- or 4-pyridylmethyl, 4-(2-thienyl)propyl, 1- or 5-tetrazolylmethyl, 2-benzothiazolyl methyl, 2-benzoxazolylmethyl, 3-benzisothiazolylmethyl, 3-benzisoxazolylmethyl, 2-(1-piperidinyl)ethyl or the like.

When $R^2$ is a N-containing heterocyclic group whose N-atom is attached to the carbonyl carbon atom of the acyl group —$COR^2$, such heterocyclic group is invariably combined to the carbonyl through the above-mentioned alkylene chain. As examples of such heterocycle-alkyl group having an alkylene chain attached to the N-atom, there may be mentioned 1-pyrrolylmethyl, 2-oxo-1-pyrrolidinylmethyl, 1-imidazolylmethyl, 3,5- dimethyl-1-pyrazolylmethyl, 1-piperidylethyl, 4-morpholinylmethyl, 1-tetrazolylmethyl, 2,5-dioxo-1-pyrrolidinylmethyl, 1,3-dioxo-2-isoindolylmethyl, 2-thioxo-4-oxo-3-thiazolidinylmethyl, 3,5-diiodo-4-oxo-1,4-dihydropyridine-1-methyl, 4-methyl-1-piperazinyl-methyl, 1-indolylethyl or the like.

The N-acyl-α-aminoacyl group represented by the formula (B) will now be described.

The alkyl, alkenyl, cycloalkyl, cycloalkenyl, aryl or heterocyclic group as represented by $R^3$, $R^4$, or $R^5$ may be the same as those mentioned for $R^2$. These groups as well as indolyl and imidazolyl may optionally be substituted and such substituents may be the same as those mentioned in connection with $R^2$. When the cyclic group $R^3$, $R^4$ or $R^5$ (i.e. cycloalkyl, cycloalkenyl, aryl or heterocyclic group, inclusive of indolyl and imidazolyl) may be attached, directly or through an alkylene chain, to the α-carbon atom, N-atom or the carbonyl group on the N-atom in the formula (B) and such alkylene chain may be the same as those mentioned hereinbefore in connection with $R^2$.

The alkoxy group $R^5$ may be an alkoxy of about 1 to 4 carbon atoms (e.g. methoxy, ethoxy, propoxy, isopropoxy, butoxy, isobutoxy, sec-butoxy, tert-butoxy).

Referring, further, to the formula (B), the N-acyl-α-aminoacyl group is typically exemplified by N-acetyl-N-methyl-glycyl, N-benzoyl-N-methyl-glycyl, N-(4-chlorobenzoyl)-N-methyl-glycyl, N-acetyl-N-methyl-alanyl, N-acetyl-N-benzyl-alanyl, N-acetyl-N-methyl-leucyl, N-isobutylyl-N-methyl-alanyl, N-isovaleryl-N-methyl-alanyl, N-propionyl-N-methyl-alanyl, N-acetyl-N-methyl-phenylalanyl, 2-(N-acetyl-N-methyl)-3-methoxycarbonylpropionyl, 2-(N-acetyl-N-methyl)-3-methylmercaptopropionyl, 2-(N-acetyl-N-methyl)-3-ethylmercaptopropionyl, $N^\alpha$-acetyl-$N^\alpha$, N'-dimethyl-histidinyl, N-acetyl-N-methylisoleucyl, N-acetyl-N-methyl-leucyl, N-acetyl-N-methyl-methionyl, N-acetyl-N-methyl-phenylalanyl, N-acetyl-N-methyl-tryptophanyl, N-acetyl-N-methyl-4'-acetoxy-tyrosinyl, N-benzyl-N-methyl-valyl, N-acetyl-N-methyl-phenylglycyl, N-isonicotinoyl-N-methyl-α-aminobutyryl, N-acetyl-N-methyl-3-cyanoalanyl, N-acetyl-N-methyl-α-(2-thiazolyl)glycyl, N-acetyl-N-methyl-(4'-dimethylamino)phenylalanyl, etc.

In the above-mentioned R of the compound (I), desirable is an acyl group of the formula (A) wherein $R^2$ is H, $C_{1-18}$ alkyl, $C_{2-10}$ alkenyl, $C_{3-10}$ cycloalkyl, $C_{3-10}$ cycloalkenyl, phenyl, naphthyl or, 4-, 5- or 6-membered heterocyclic group containing N, O or/and S which may have a fused benzene ring, any of said groups being unsubstituted or substituted by $C_{1-4}$ alkyl, $C_{1-4}$ alkoxy, $C_{2-4}$ alkanoyl, $C_{2-4}$ alkanoyloxy, $C_{2-4}$ alkoxycarbonyl, halogen, nitro, cyano, trifluoromethyl, di-$C_{1-4}$ alkylamino, $C_{1-4}$ alkylthio, methylsulfinyl, methylsulfonyl, oxo, thioxo or $C_{1-4}$ alkanoylamido, and said cycloalkyl, cycloalkenyl, phenyl, naphthyl and heterocyclic groups being attached, directly or through $C_{1-4}$ alkylene, to the carbonyl group in the acyl R, and more desirable is an acyl group of the formula (A) wherein $R^2$ is $C_{1-6}$ alkyl, $C_{3-7}$ cycloalkyl, phenyl or pyridyl, said alkyl being unsubstituted or substituted by halogen, and said cycloalkyl, phenyl and pyridyl being optionally attached, directly or through $C_{1-4}$ alkylene, to the carbonyl group in the acyl R.

Alternatively, in the above-mentioned R of the compound (I), desirable is a N-acyl-α-aminoacyl group of the formula (B) wherein $R^3$ is H, $C_{1-18}$ alkyl, $C_{3-10}$ cycloalkyl, phenyl, naphthyl, indolyl or imidazolyl, $R^4$ is H, $C_{1-18}$ alkyl, $C_{3-10}$ cycloalkyl, phenyl or naphthyl, and $R^5$ is H, $C_{1-18}$ alkyl, $C_{2-10}$ alkenyl, $C_{3-10}$ cycloalkyl, phenyl, naphthyl or, 4-, 5- or 6-membered heterocyclic group containing N, O or/and S which may have a fused benzene ring, any of said groups in $R^3$, $R^4$ and $R^5$ being unsubstituted or substituted by at least one $C_{1-4}$ alkyl, $C_{1-4}$ alkoxy, $C_{2-4}$ alkanoyl, $C_{2-4}$ alkanoyloxy, $C_{2-4}$ alkoxycarbonyl, halogen, nitro, cyano, trifluoromethyl, di-$C_{1-4}$ alkylamino, $C_{1-4}$ alkylthio, methylsulfinyl, methylsulfonyl, oxo, thioxo or $C_{1-4}$ alkanoylamido, and said cycloalkyl, cycloalkenyl, phenyl, naphthyl and heterocyclic groups including indolyl and imidazolyl in $R^3$, $R^4$ and $R^5$ being attached, directly or through $C_{1-4}$ alkylene to the α-carbon atom, N-atom or the carbonyl group on the N-atom in the N-acyl-α-aminoacyl R, and more desirable is a N-acyl-α-aminoacyl group of the formula (B) wherein $R^3$, $R^4$ and $R^5$ are $C_{1-6}$ alkyl.

The dechloromaytansinoid compound (I) wherein R is hydrogen, that is dechloromaytansinol of formula (Ia);

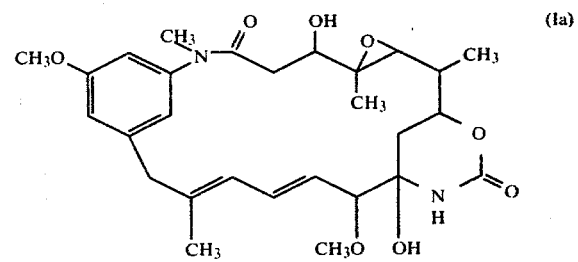

can be produced by reducing a compound of formula (II):

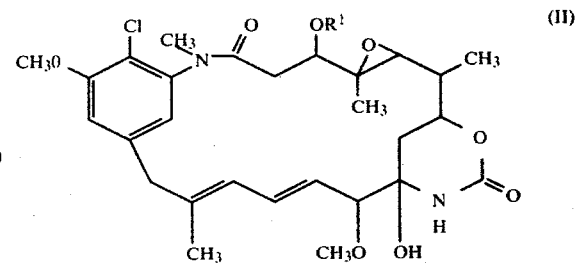

wherein $R^1$ is acyl, with a metal hydride.

Referring to the above general formula (II), the acyl group $R^1$ has the same meaning as defined in connection with R.

The metal hydride mentioned just above may for example be a metal complex hydride, preferably lithium aluminum hydride (LAH). The amount of such metal hydride, based on starting compound (II), is normally within the range of about 1 to 25 molar equivalents and preferably about 4 to 10 molar equivalents. This reduction reaction is normally expediently conducted in a solvent. The solvent includes, for example, ethers (e.g. diethyl ether, tetrahydrofuran, etc.), tetrahydrofuran being especially desirable. The reaction is normally carried out at a temperature of about −70° C. to about +80° C. and preferably about −40° C. to about +20° C. In many instances this reaction yields as a by-product a compound (II) with the 3-acyl group having been removed, i.e. maytansinol. After this reduction reaction, the excess reducing agent is decomposed by the addition of water, acetic acid, ethyl acetate or the like and after the reaction mixture is made acidic, it is extracted with a suitable solvent (e.g. ethyl acetate). This crude product is purified by silica gel column chromatography or high pressure liquid chromatography to obtain the desired compound dechloromaytansinol.

The dechloromaytansinoid compound (I) wherein R is acyl, that is the compound having the formula (Ib);

(Ib)

wherein $R^1$ is acyl can be produced by reacting dechloromaytansinol with a carboxylic acid of the formula (III):

$$R^1-OH \quad (III)$$

wherein $R^1$ has the same meaning as defined above, or a reactive derivative thereof with respect to its carboxyl function.

Referring to the above formulas (Ib) and (III), the acyl group $R^1$ is the same as the acyl group in the above-mentioned R.

A typical acylation process comprises acylating dechloromaytansinol with carboxylic acid (III) in the presence of a carbodiimide.

Based on dechloromaytansinol, the carboxylic acid (III) may be used for example in a proportion of about 1 to 500 molar equivalents and, in many cases, preferably in a proportion of about 1 to 30 equivalents.

The carbodiimide may be used, based on dechloromaytansinol, in a proportion of about 1 to 700 molar equivalents and, in many cases, preferably in a proportion of about 1 to 50 equivalents. The carbodiimide compound which can be used for the production of compounds of this invention need only contain a carbodiimide bond (—N=C=N—) which is transformable into a urea bond (—NH—CO—NH—) in the course of the present acylation reaction. Thus, compounds represented by the following formula, for instance, may be utilized.

$$R^6-N=C=N-R^7 \quad (IV)$$

wherein $R^6$ and $R^7$ each represents an organic acid residue such that its carbodiimide bond is transformable into a urea bond during the acylation reaction.

The organic residues $R^6$ and $R^7$ may be selected from among $C_{3-7}$ cycloalkyl groups optionally having di-lower ($C_{1-6}$; the same definition applies hereinafter) alkylamino; a lower alkyl group optionally substituted by di-lower alkylamino or morpholino; and a phenyl group optionally substituted by lower alkyl. The carbodiimide is preferably dicyclohexylcarbodiimide DCC for practical purposes, although use may likewise be made of other carbodiimides such as diphenylcarbodiimide, di-o-tolylcarbodiimide, di-p-tolylcarbodiimide, di-tert-butylcarbodiimide, 1-cyclohexyl-3-(2-morpholinoethyl)carbodiimide, 1-cyclohexyl-3-(4-diethylaminocyclohexyl)carbodiimide, 1-ethyl-3-(2-diethylaminopropyl)carbodiimide and 1-ethyl-3-(3-dimethylaminopropyl)carbodiimide.

This acylation reaction may be carried out in the presence of a suitable solvent. Among such solvents are esters (e.g. ethyl acetate), ethers (e.g. diethyl ether, dioxane, tetrahydrofuran), halogenated hydrocarbons (e.g. dichloromethane, chloroform), nitriles (e.g. acetonitrile), aromatic hydrocarbons (e.g. benzene), nitromethane, pyridine, dimethylformamide, dimethylsulfoxide, sulfolane, etc. and suitable mixtures of such solvents.

This reaction may be usually carried out at a suitable temperature from ice-cooling to the reflux point of the reaction system.

This acylation reaction can be advantageously hastened with the aid of a catalyst capable of promoting acylation of dechloromaytansinol. The catalyst may be an appropriate acid or base. The basic catalyst includes, among others, tertiary amine compound (e.g. aliphatic tertiary amines such as triethylamine; aromatic tertiary amines such as pyridine, α-, β-, or γ-picoline, 2,6-lutidine, 4-dimethylaminopyridine, 4-(1-pyrrolidinyl)pyridine, dimethylaniline, diethylaniline), halogenated alkali metals (e.g. potassium fluoride, anhydrous lithium iodide), salts of organic acids (e.g. sodium acetate) and so forth. The acid catalyst includes, among others, Lewis acids [e.g. anhydrous zinc chloride, anhydrous aluminum chloride ($AlCl_3$), anhydrous ferric chloride, titanium tetrachloride ($TiCl_4$), stannic tetrachloride ($SnCl_4$), antimony pentachloride, cobalt chloride, cupric chloride, boron trifluoride etherate, etc.], inorganic strong acids (e.g. sulfuric acid, perchloric acid, hydrochloric acid, hydrobromic acid, etc.), organic strong acids (e.g. benzenesulfonic acid, p-toluenesulfonic acid, trifluoroacetic acid, trichloroacetic acid, etc.), acidic ion exchange resins (e.g. polystyrene-sulfonic acid), etc.

When a carboxylic acid (III) having an acyl group of formula (A) is employed, 4-dimethylaminopyridine or 4-(1-pyrrolidinyl)pyridine is particularly desirable and when a carboxylic acid (III) having an N-acyl-α-aminoacyl group (B) is employed, anhydrous zinc chloride is a preferred catalyst.

The catalyst is used in a catalytic amount sufficient to promote acylation of dechloromaytansinol with carboxylic acid (III), e.g. about 0.001 to about 10 molar equivalents, preferably about 0.01 to about 1 equivalent, based on carboxylic acid (III). The use of such a catalyst leads in many cases to remarkably improved yields of compound (Ib). The amount of carboxylic acid may also be reduced. Thus, in many cases, the relative amount of (III) with respect to dechloromaytansinol may be reduced to about 1 to 10 molar equivalents.

In connection with this reaction, if the carboxylic acid (III), such as a carboxylic acid having an N-acyl-α-aminoacyl group (B), is isomeric, i.e. D- and L-isomers, such isomers of (III) may be employed either independently or as an optional mixture. When an optically active acyl group is introduced into the 3-hydroxyl group of dechloromaytansinol, the use of the corresponding optical form of carboxylic acid (III) proves advantageous in some instances. There also are cases in which even the use of an optically active carboxylic acid (III) gives rise to a mixture of D- and L-isomers of compound (Ib).

The acylation process utilizing a reactive derivative of carboxylic acid (III) with respect to its carboxyl function may for example be a process which comprises using a derivative having a functional group capable of acylating the 3-position of dechloromaytansinol such as the acid anhydride of carboxylic acid (III). The solvent and catalyst for use in this acylation reaction may be the same as those mentioned hereinbefore in connection with acylation in the presence of a carbodiimide. The reaction temperature may usually range from about $-20°$ C. to about $+100°$ C. and preferably about $20°$ C. to about $40°$ C. The reaction may be hastened by heating the reaction system to a still higher temperature.

The compound (Ib) thus produced can be isolated by subjecting the reaction mixture to a conventional procedure such as concentration, solvent extraction, chromatography, recrystallization, etc. When compound (Ib) is produced as a mixture of isomers (e.g. D- and L-isomers), the isomers can be separated from each other generally by a conventional procedure, e.g. silica gel column chromatography. The dechloromaytansinoid compound (I) according to this invention includes such individual isomers and all mixtures of the isomers.

The dechloromaytansinoid compound (I), especially (Ib), according to this invention has strong anti-mitotic activity and antitumor activity, with comparatively low toxicity and therefore can be orally or parenterally administered by tumor-bearing warm blooded animals (e.g. mouse, rat, rabbit, dog, cat, human being) for prolongation of their survival time.

The compound (I) is normally administered in the form of a suitable pharmaceutical preparation (e.g. injectable preparation) as formulated with a conventional carrier, diluent or the like.

When compound (I) is administered in the form of an injectable preparation, it may be given subcutaneously, intraperitoneally, intravenously or intramuscularly, for instance. The dosage of compound (I) varies with the kind, symptom, administration route, etc. but, for example, in case of intravenous administration for prolonging life span of the animal suffering from leukemia or melanoma, it may be decided from the range of about 1 to 1000 µg/kg body weight, preferably about 10 to 500 µg/kg body weight, especially about 25 to 400 µg/kg body weight, per dose.

Such an injectable solution can be prepared by the established pharmaceutical procedure, e.g. by dissolving about 50 µg to 3 mg of (I) in about 0.5 ml of alcohol (e.g. ethanol) and making up the solution with physiological saline to obtain a total of 10 ml. When only a small dose is indicated, the above solution may be further diluted with physiological saline.

The dechloromaytansinoid compound (I) is useful also in that it displays antifungal and antiprotozoal activities. Thus, for example, the compound (I) is useful for treating *Tetrahymena pyriformis W*. When (I) is used as an antifungal or/and antiprotozoal agent, it proves advantageous in testing a sample of soil, active sludge or animal body fluid for its bacterial flora. Thus, in such applications as the isolation of useful bacteria from soil samples and an assay of the activity of bacteria, to the exclusion of protozoa and fungi, in the operation and analysis of active sludge systems for waste water treatment, the compound (I) specifically allows the bacteria to grow without permitting growth of fungi and protozoa which may also be present in the specimens. A typical such procedure may comprise adding a test specimen to a liquid or solid medium, then adding 0.1 ml of about 10 to 100 µg/ml of compound (I) in water with 1% methanol added and incubating the mixture.

The dechloromaytansinoid compound (I), at the dose level of 0.02 ml as a 1 mg/ml aqueous solution, inhibits growth of the causative microorganisms of stem rot, Helminthosporium leaf spot and sheath blight in rice plants and, therefore, can be used in the control of such plant diseases by spraying rice plants with a solution of compound (I) in 1% methanol-water, the concentration of which may range from about 0.5 to 5 µg/ml.

The starting compound (II) employed in the method of this invention may be one of the known compounds such as maytansines and ansamitocins, and may also be produced by acylating maytansinol with said carboxylic acid of formula (III) or said reactive derivative of (III) with respect to its carboxyl function. The acylation process may be similar to that described hereinbefore in connection with the acylation of dechloromaytansinol.

Maytansinol, the starting compound (II) for the production of the compounds according to this invention, is a known compound and a plant principle [Kupchan et al., J. Amer. Chem. Soc., 97, 5294 (1975)]. It can also be produced by reductive cleavage of maytancine and its analogs.

Maytansinol can also be produced advantageously by growing an Antibiotic C-15003—producing strain of the genus Nocardia (FERM-P No. 3992, IFO-13726, ATCC-31281) in a culture medium to obtain ansamitocin of formula (V):

wherein $R^8$ is acetyl, propionyl, isobutyryl, n-butyryl or isovaleryl, and subjecting the same [V] to reductive cleavage with a metal hydride such as LiAlH₄ [E. Higashide et al, Nature, vol. 270, 721 (1977); U.S. Pat. No. 4,162,940 (Ser. No. 811,448)]

The starting compound (III) for the production of compounds of this invention is generally a carboxylic acid which is known per se or a carboxylic acid produced by a process analogous to the known process for the production of such known carboxylic acids. The following is a partial list of the available literature on such known production methods.

J. R. Coggins, N. L. Benoiton, Can. J. Chem., 49, 1968 (1971),

P. Quitt, J. Hellerback, K. Vogler, Helv. Chim. Acta, 46, 327 (1963),

S. L. Portnova, et al, Zh, Obsch. Khim., 38, 428(1968)

The following examples are intended to describe this invention in further detail and not to limit its scope.

EXAMPLE 1

In 800 ml of dry tetrahydrofuran (THF) is dissolved 15.0 g of Ansamitocin antibiotic mixture (12% of ansamitocin P-2, 71% of P-3 and 17% of P-4) and under dry nitrogen gas streams, the solution is cooled to $-50°$ C. in a dry ice-acetone bath. Then, 13.0 g of lithium aluminum hydride (LAH) is added in a single dose and the mixture is stirred at $-50°$ C. to $-22°$ C. for 2 hours. Then, at $-28°$ C., a further 3 g of LAH is added and the reaction mixture is stirred at $-28°$ C. to $-22°$ C. for 80 minutes. Thereafter, at $-50°$ C., 750 ml of 2 N HCl is added dropwise with caution and the reaction mixture is extracted three times with 2.6 l, 1.6 l and 0.8 l portions of ethyl acetate. The extracts are pooled, washed with a saturated aqueous solution of sodium chloride (100 ml×2) and dried (MgSO$_4$, 250 g). The solvent is distilled off under reduced pressure and the residue (13.6 g) is chromatographed on a column of silica gel (1.2 kg), elution being carried out with ethyl acetate-water (98.5:1.5, V/V). The eluate is collected in 400-gram fractions. Fractions 35 through 52 are pooled, the solvent distilled off and the residue dried in vacuo to obtain 7.25 g of maytansinol. Then, fractions 53 through 68 are similarly treated to obtain 1.55 g of a substantially equimolar mixture of maytansinol and dechloromaytansinol. Similarly, fractions 69 through 86 yield 0.78 g of dechloromaytansinol.

This product is reprecipitated from chloroform-hexane to obtain 0.71 g of dechloromaytansinol.

m.p. 174°-179° C. (decompn.)

NMR spectrum (CDCl$_3$) δppm: 0.86(3H, s), 1.27(3H, d, J=ca. 6 Hz), 1.65(3H, s), 2.63(1H, d, J=9 Hz), 9.07(1H, d, J=13 Hz), 3.23(3H, s), 3.35(3H, s), 3.42(1H, d, J=13 Hz), 3.75(1H, d, J=9 Hz), 3.81(3H, s), 4.37(1H, m), 5.51(1H, dd, J=9 Hz & 15 Hz), 6.10(1H, d, J=11 Hz), 6.41(1H, dd, J=11 Hz & 15 Hz), 6.56(1H, d, J=2 Hz), 6.60(1H, s), 6.70(1H, approx. s), 6.97(1H, approx. s), Mass spectrum (m/e): 469, etc.

UV spectrum ($\lambda_{max}^{MeOH}$) nm: 281.5, 241.5, 250.5, 277.5, 286.

EXAMPLE 2

The procedure described in Example 1 was substantially repeated, except that:

In 700 ml of THF, 13.1 g of D-maytansine is reduced at $-40°$ C. to $-20°$ C. for 3 hours, using 11.5 g of LAH and, then, with 2.5 g of LAH. Then, 650 ml of 2 N HCl is added and the mixture is extracted with ethyl acetate (3 times; 2.4 l, 1.4 l, 0.7 l). The extracts are pooled, washed and dried, and the solvent is distilled off to obtain 7.1 g of crude product. As in Example 1, this crude product is chromatographed and 3.6 g of maytansinol is obtained from fractions 22 through 52. The subsequent 7 l portion of the eluate yields 0.42 g of a substantially equimolar mixture of maytansinol and dechloromaytansinol. The further subsequent 9 l portion yields 0.50 g of dechloromaytansinol. In TLC and NMR spectrum, this dechloromaytansinol was identical with the compound according to Example 1.

EXAMPLE 3

In 15 ml of dry dichloromethane is dissolved 100.0 mg (0.189 mmol) of dechloromaytansinol, followed by the addition of 69 mg (0.476 mmol) of N-acetyl-N-methyl-L-alanine, 117 mg (0.568 mmol) of DCC and 39 mg (0.287 mmol) of anhydrous zinc chloride. The mixture is stirred at room temperature (ca 23° C.) for 30 minutes at the end of which time 55 mg (0.379 mmol) of N-acetyl-N-methyl-L-alanine, 98 mg (0.476 mmol) of DDC and 31 mg (0.228 mmol) of anhydrous zinc chloride are further added. The mixture is stirred at room temperature for a 2 additional hours. The insoluble fraction is removed by filtration, the filtrate washed with water, dried and concentrated to dryness. The residue is dissolved in 30 ml of ethyl acetate, the insolubles filtered off, the filtrate concentrated to dryness and the residue dissolved in about 5 ml of ethyl acetate. The solution is chromatographed on a column of silica gel [25 mm (out.dia.), 500 mm] and elution is carried out first with ethyl acetate/H$_2$O-saturated ethyl acetate (2:1, V/V) and then with H$_2$O-saturated ethyl acetate, the eluate being collected in 15-g fractions. Fractions 55 through 103 are combined and the solvent is distilled off, whereby 53 mg of crude dechloromaytansine is obtained. This crude product is dissolved in ethyl acetate, ether is added and the solution is cooled. By the above procedure is obtained 24 mg of dechloromaytansine as white crystals.

m.p. 184°-186° C. (decompn.)

NMR spectrum (CDCl$_3$) δ ppm: 0.85 (3H, s), 1.29(3H, d, J=ca. 5 Hz), 1.32(3H, d, J=7 Hz), 1.64(3H, s), 2.06(3H, s), ca. 2.13(1H, dd, J=3 Hz & 15 Hz), ca. 2.82(1H, dd, J=12 Hz & 15 Hz), 2.83(3H, s), 3.03(1H, d, J=9 Hz), 3.22(1H, (d), (J=13 Hz)), 3.25(3H, s), 3.36(3H, s), 3.49(1H, d, J=ca. 9 Hz), 3.61(1H, (d), (J=13 Hz)), 3.87(3H, s), 4.27(1H, m), 4.80(1H, dd, J=3 Hz & 12 Hz), 5.32(1H, q, J=7 Hz), 5.69(1H, dd, J=9 Hz& 14 Hz), 6.33(1H, broad), ca. 6.35(1H, dd, J=ca. 11 Hz & ca. 14 Hz), ca. 6.64(1H, d, J=ca. 11 Hz), ca. 6.53(2H, m), 6.67(1H, t, J=ca. 1.5 Hz), etc.

Mass spectrum (m/e): 596, etc.

UV spectrum ($\lambda_{max}^{MeOH}$) nm: 232, 241.5, 251, 277, 285.5.

Fractions 168 through 221 of the above chromatographic eluate are pooled and the solvent is distilled off to recover 65 mg of D-dechloromaytansine. This product is dissolved in chloroform, ether is added and the resulting crystals are collected by filtration. The above procedure yields 21 mg of D-dechloromaytansine as colorless fine crystals.

m.p.: 175°-178° C. (decompn.)

NMR spectrum (CDCl$_3$) δ ppm: 0.91(3H, s), 1.27(3H, d, J=5 Hz), 1.48(3H, d, J=7.5 Hz), 1.68(3H, s), 2.13(3H, s), 2.16 (1H, dd, J=3 Hz & 14 Hz), 2.82(1H, d, J=ca. 9 Hz), ca. 2.91 (1H, (dd)), 3.02(3H, s), 3.20(3H, s), 3.32(3H, s), 3.43(1H, d, J=9 Hz), 3.46(1H, d, J=13 Hz), 3.83(3H, s), 4.28(1H, m), 4.86(1H, dd, J=ca. 3 Hz & ca. 14 Hz), 4.91(1H, q, J=7.5 Hz), 5.5-5.8(1H, broad), 5.78(1H, dd, J=9 Hz & 14 Hz), 6.13(1H, d, J=11 Hz), 6.30(1H, broad), 6.44(1H, dd, J=11 Hz & 14 Hz), 6.57(1H, t, J=ca. 2 Hz), 6.68(1H, t, J=ca. 2 Hz), 6.75(1H, t, J=ca. 2 Hz), etc.

Mass spectrum (m/e): 657, 596.

UV spectrum ($\lambda_{max}^{MeOH}$) nm: 231, 240.5, 251, 277, 285.

EXAMPLE 4

In 10 ml of dry dichloromethane is dissolved 90 mg (0.170 mmol) of dechloromaytansinol, followed by the addition of 280 mg (1.772 mmol) of isobutyric anhydride and 44 mg (0.361 mmol) of 4-dimethylaminopyridine (DMAP). The mixture is stirred at room temperature for 1.5 hours, after which 22 mg (0.180 mmol) of DMAP is further added. The mixture is stirred at the same temperature for 17 hours. The reaction mixture is washed with 0.5 N HCl (10 ml×2), aqueous sodium hydrogen carbonate (10 ml) and water (10 ml×2) in the order mentioned, followed by drying. The solvent is distilled off, the residue (174 mg) dissolved in chloroform and the solution chromatographed on a column of silica gel [20 mm (out.dia.)×400 mm], elution being carried out with chloroform-ethanol (100:1 to 40:1). The eluate is collected in 25-g fractions. Fractions 42 through 65 are pooled and the solvent is distilled off, whereupon 69 mg of crude dechloromaytansinol 3-isobutyrate is obtained. This product is dissolved in ethyl acetate, the solution allowed to stand and the resulting crystals collected by filtration. By the above procedure is obtained 44 mg of dechloromaytansinol 3-isobutyrate as white prisms.

m.p. 250°–252° C. (decompn.)

NMR spectrum (CDCl$_3$) δ ppm: 0.81(3H, s), 1.17(3H, d, J=6 Hz), 1.18(3H, d, J=6 Hz), 1.25(3H, d, J=6 Hz), 1.70(3H, s), 2.18(1H, dd, J=3 Hz & ca. 14 Hz), 2.55(1H, m), 2.75(1H, dd, J=11 Hz & ca. 14 Hz), 2.91(1H, d, J=9 Hz), 3.15(1H, d, J=ca. 13 Hz), 3.23(3H, s), 3.36(3H, s), 3.47(1H, d, J=9 Hz), 3.48(1H, d, J=ca. 13 Hz), 3.4–3.6(1H, broad), 3.84(3H, s), 4.26 (1H, m), 4.83(1H, dd, J=3 Hz & 11 Hz), 5.46(1H, dd, J=9 Hz & 15 Hz), 6.12(1H, d, J=11 Hz), 6.45(1H, dd, J=11 Hz & 15 Hz), 6.60(1H, d, J=2 Hz), 6.64(1H, s), 6.76(2H, d, J=2 Hz), etc.

Mass spectrum (m/e): 600, 557, 539, 524, etc.

UV spectrum ($\lambda_{max}^{MeOH}$) nm: 232.5, 241, 251, 277.5, 285.5.

EXAMPLE 5

In 10 ml of dry dichloromethane are dissolved 100.8 mg of dechloromaytansinol, 141.5 mg of nicotinic acid and 291.0 mg of DCC and, after 10 minutes, 50.2 mg DMAP is added. The mixture is stirred at room temperature for 4 hours. The solvent is distilled off, the residue dissolved in a small amount of ethyl acetate and the insolubles filtered off. The filtrate is concentrated, the residue dissolved in ethyl acetate again, the insolubles filtered off, the filtrate is concentrated and the residue chromatographed on 75 g silica gel (solvent: H$_2$O-saturated ethyl acetate), the eluate being collected in 20-g fractions. Fractions 18 through 37 are pooled and the solvent is distilled off to obtain 88.6 mg of crude product. This product is chromatographed on silica gel (12 g) in the same manner as above and fractions 6 through 11 are treated to obtain 75.7 mg of product. This product is recrystallized from ethyl acetate-ether. By the above procedure is obtained 55.0 mg of dechloromaytansinol 3-nicotinate.

m.p. 170°–173° C. (decompn.)

NMR spectrum (CDCl$_3$) δ ppm: 0.92(3H, s), 1.30(3H, d, J=5 Hz), 1.70(3H, s), 2.36(1H, dd, J=3 Hz & 14 Hz), 2.96(1H, dd, J=12 Hz & 14 Hz), 3.04(1H, d, J=9 Hz), 3.20(3H, s), 3.24(3H, s), 3.36(1H, d, J=9 Hz), 3.60(1H, d, 13 Hz), 3.86(3H, s), 4.20(1H, m), 4.90(1H, dd, J=9 Hz & 14 Hz), 5.19(1H, dd, J=3 Hz & 12 Hz), 6.15(1H, d, J=12 Hz), 6.37(1H, dd, J=12 Hz & 14 Hz), 6.65(1H, t, J=2 Hz), 6.83(2H, m), 7.44(1H, m), 8.31(1H, m), 8.82(1H, m), 9.29(1H, m), etc.

Mass spectrum (m/e): 574, 559, 546, 542, 532, 494.

EXAMPLE 6

In dry dichloromethane are dissolved 88.1 mg of dechloromaytansinol, 119 mg of cyclohexanecarboxylic acid and 231.1 mg of DCC and, after 10 minutes, 47.9 mg of DMAP is added. The mixture is stirred at room temperature overnight. Then, 0.05 ml of cyclohexanecarboxylic acid, 130 mg of DCC and 19.3 mg of DMAP are added. The mixture is again stirred at the same temperature overnight. The solvent is then distilled off, the residue dissolved in ethyl acetate and the insolubles filtered off. The filtrate is washed twice with 0.5 N HCl and, then, with aqueous sodium hydrogen carbonate, followed by drying (over Na$_2$SO$_4$). The solvent is distilled off and the residue is chromatographed on a column of silica gel (75 g) (solvent: ethyl acetate), the eluate being collected in 20-g fractions. Fractions 16 through 32 are pooled and the solvent is distilled off, whereby 47.7 mg of crude product is obtained. This crude product is rechromatographed on 35 g of silica gel and fractions 9 through 20 are treated in the same manner as above to obtain 36.5 mg of product. This product is recrystallized from ethyl acetate-ether. The above procedure yields 24.6 mg of dechloromaytansinol 3-cyclohexanecarboxylate.

m.p. 217°–220° C. (decompn.)

NMR spectrum (CDCl$_3$) δ ppm: 0.85(3H, s), 1.24(3H, d, J=5 Hz), 1.70(3H, s), 2.26(1H, dd, J=3 Hz & 14 Hz), 2.74(1H, dd, J=11 Hz & 14 Hz), 2.88(1H, d, J=9 Hz), 3.16(1H, d, J=12 Hz), 3.20(3H, s), 3.37(3H, s), 3.49(1H, d, J=9 Hz), 3.50(1H, d, J=13 Hz), 3.85(3H, s), 4.26(1H, m), 4.87(1H, dd, J=3 Hz & 11 Hz), 5.46(1H, dd, J=9 Hz & 15 Hz), 6.13(1H, d, J=12 Hz), 6.47(1H, dd, J=12 Hz & 15 Hz), 6.61(1H, approx. d, J=2 Hz), 6.70(2H, d, J=2 Hz), etc.

Mass spectrum (m/e): 640, 625, 622, 597, 579, 564, 551, 547.

EXAMPLE 7

In 10 ml of dry dichloromethane are dissolved 110.7 mg of dechloromaytansinol, 169.6 mg of phenylacetic acid, 302.0 mg of DCC and 52.0 mg of DMAP. The solution is stirred at room temperature for 3.5 hours, the insolubles are filtered off and the filtrate is treated and chromatographed (silica gel 75 g) as in Example 6. Fractions 16 through 35 yields 96.8 mg of product, which is recrystallized from ethyl acetate-ether. By the above procedure is obtained 67.2 mg of dechloromaytansinol 3-phenylacetate.

m.p. 165°–170° C. (decompn.)

NMR spectrum (CDCl$_3$) δ ppm: 0.86(3H, s), 1.25(3H, d, J=6 Hz), 1.67(3H, s), 2.11(1H, dd, J=3 Hz & 14 Hz), 2.68(1H, dd, J=11 Hz & 14 Hz), 2.93(1H, d, J=9 Hz), 3.07(3H, s), 3.37 (3H, s), 3.52(1H, d, J=9 Hz), 3.74(2H, AB-quartet, J$_{AB}$=ca. 14.5 Hz), 3.83(3H, s), 4.29(1H, m), 4.99(1H, dd, J=3 Hz & 11 Hz), 5.64(1H, dd, J=9 Hz & 14 Hz), 6.07–6.78(6H, m), etc.

EXAMPLE 8

In 5 ml of dry dichloromethane are dissolved 66.8 mg of dechloromaytansinol, 215.5 mg of monochloroacetic anhydride, 182 mg of DCC and 92.2 mg of DMAP. The mixture is stirred at room temperature for 30 minutes, the insolubles are filtered off and the filtrate is dried under reduced pressure. The residue is dissolved in ethyl acetate and the insolubles are filtered off. The filtrate is washed with 1 N HCl, saturated aqueous sodium hydrogen carbonate and water in the order mentioned, and dried (Na$_2$SO$_4$). The solvent is distilled off and the residue is chromatographed on a column of silica gel (SiO$_2$, 40 g), elution being carried out with ethyl acetate/H$_2$O-saturated ethyl acetate (6:1, V/V). The eluate is collected in 15-g fractions, fractions 10 through 21 are combined and the solvent is distilled off, whereby 54.0 mg of dechloromaytansinol 3-chloroacetate is obtained.

m.p. 205°–207° C. (decompn.)

Mass spectrum (m/e): 606 (M+), 545(M+-61).

Experimental Data

Antitumor Activity

Therapeutic tests were carried out in mice according to NCI-protocols 1,200 and 1,300, Cancer Chemother, Reports, Part 3, 1972, Vol. 3, No. 2, in which leukemia P-388 and melanoma B-16 tumor cells had been intraperitoneally transplanted, compound (I) being administered intraperitoneally once daily for 9 consecutive days. Life span prolongations obtained are shown in Table 1 as T/C % values.

TABLE 1

| Compound | Dose ($\mu$g/kg) | Antitumor activities P-388 (T/C %) | B-16 (T/C %) |
|---|---|---|---|
| Dechloromaytansinol 3-isobutyrate | 800 | | 214 |
| | 400 | 224 | 174 |
| | 200 | 193 | 152 |
| | 100 | 189 | 150 |
| | 50 | 168 | |
| Dechloromaytansine | 800 | | 190 |
| | 400 | 189 | 179 |
| | 200 | 175 | 152 |
| | 100 | 165 | 171 |
| | 50 | 158 | |

Antiprotozoal Activity

Antiprotozoal activity of compound (I) was assayed with *Tetrahymena pyriformis* W as the test organism and a medium composed of 20 g tryptose-peptone (Difco Co.), 1 g yeast extract, 2 g glucose, 1000 ml distilled water, 10 ml 1 M phosphate buffer (pH 7.0) as the assay medium. The microorganism was incubated at 28° C. for 44 to 48 hours and the growth inhibitory activity of compound (I) was assayed by the serial dilution method. The minimal inhibitory concentrations of compound (I) are shown in Table 2.

TABLE 2

| Compound | Antiprotozoal activity MIC ($\mu$g/ml) *Tetrahymena pyriformis* |
|---|---|
| Compound Dechloromaytansinol 3-phenylacetate | 2 |
| Dechloromaytansinol 3-cyclohexane carboxylate | 4 |
| Dechloromaytansinol 3-chloroacetate | $\geq 4$ |

EXAMPLES OF PHARMACEUTICAL COMPOSITIONS

Example A

Composition for Injection

| | |
|---|---|
| (1) Dechloromaytansinol 3-isobutyrate | 200 mg |
| (2) Ethanol | 10 g |
| (3) Polysorbate 80 (Tween 80) | 40 g |
| (4) Mannitol | 20 g |
| (5) Distilled water, a sufficient quantity | |
| to make | 1000 ml |

Preparation (1) is dissolved in (2). To this solution, (3) and (4) are added, followed by the addition of sterilized distilled water to make 1000 ml of the solution. Ten milliliter each of the solution is used to fill 100 amber ampoules and the air within the ampoules is replaced with nitrogen gas, then the ampoule is sealed. All the processes are conducted under sterile conditions.

Example B

Composition for Injection

| | |
|---|---|
| (1) Dechloromaytansine | 200 mg |
| (2) Ethanol | 5 g |
| (3) Polysorbate 80 (Tween 80) | 100 g |
| (4) Mannitol | 20 g |
| (5) Distilled water, a sufficient quantity | |
| to make | 1000 ml |

Preparation

By a similar procedure to that of Example A, an injectable solution of (1) is prepared.

What is claimed is:

1. A compound of the formula:

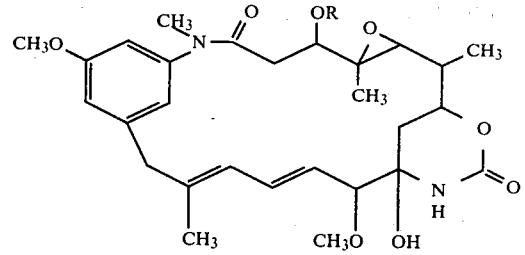

wherein R is H, acyl of the formula —COR² or acylaminoacyl of the formula

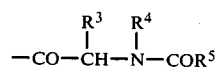

wherein R² is H or a member of the class consisting of $C_{1-18}$ alkyl, $C_{2-10}$ alkenyl, $C_{3-10}$ cycloalkyl, $C_{3-10}$ cycloalkenyl, phenyl, naphthyl or a group of the class consisting of azetidinyl, pyridyl, 1,2,3,4-tetrahydropyridyl, piperidyl, quinolyl, 1,2-dihydroquinolyl, 3- or 4-isoquinolyl, 1,2-dihydroisoquinolyl, pyrrolyl, pyrrolinyl, pyrrolidinyl, indolyl, furyl, pyranyl, dihydropyranyl, benzofuryl, benzopyranyl, thienyl, benzothienyl, imidazolyl, pyrazolyl, pyrazinyl, pyrimidyl, pyridazinyl, 2-imidazolinyl, imidazolidinyl, benzimidazolyl, indazolyl, quinoxalyl, quinazolinyl, cinnolinyl, 1,4-dioxanyl, 1,4-benzodioxanyl, 1,2- or 1,3-dithiolanyl, 1,3-dithianyl, isoxazolyl, oxazolyl, morpholinyl, benzisoxazolyl, benzoxazolyl, isothiazolyl, thiazolyl, benzisothiazolyl, benzothiazinyl, 1,2,4-, 1,2,5- or 1,3,4-oxadiazolyl, 1,2,3-, 1,2,4-, 1,2,5- or 1,3,4-thiadiazolyl, 1,2,3-, 1,2,5- or 1,3,4-triazolyl, 1,3,5-triazinyl, benzotriazolyl and 1,2,3,4-tetrazolyl, any of said R² groups being unsubstituted or substituted by $C_{1-4}$ alkyl, $C_{1-4}$ alkoxy, $C_{2-4}$ alkanoyl, $C_{2-4}$ alkanoyloxy, $C_{2-4}$ alkoxycarbonyl, halogen, nitro, cyano, trifluoromethyl, di-$C_{1-4}$ alkylamino, $C_{1-4}$ alkylthio, methylsulfinyl, methylsulfonyl, oxo, thioxo or $C_{1-4}$ alkanoylamido, and said cycloalkyl, cycloalkenyl, phenyl, naphthyl and heterocyclic groups being attached directly or through a $C_{1-4}$ alkenylene group to the carbonyl group in the acyl radical R; wherein $R^3$ is H, $C_{1-18}$ alkyl, $C_{3-10}$ cycloalkyl, phenyl, naphthyl, indolyl or imidazolyl, $R^4$ is H, $C_{1-18}$ alkyl, $C_{3-10}$ cycloalkyl, phenyl or naphthyl, and $R^5$ is H, $C_{1-18}$ alkyl, $C_{2-10}$ alkenyl, $C_{3-10}$ cycloalkyl, phenyl, naphthyl or a heterocyclic group of the class consisting of azetidinyl, pyridyl, 1,2,3,4-tetrahydropyridyl, piperidyl, quinolyl, 1,2-dihdyroquinolyl, 3- or 4-isoquinolyl, 1,2-dihydroisoquinolyl, pyrrolyl, pyrrolinyl, pyrrolidinyl, indolyl, furyl, pyranyl, dihydropyranyl, benzofuryl, benzopyranyl, thienyl, benzothienyl, imidazolyl, pyrazolyl, pyrazinyl, pyrimidyl, pyridazinyl, 2-imidazolinyl, imidazolidinyl, benzimidazolyl, indazolyl, quinoxalyl, quinazolinyl, cinnolinyl, 1,4-dioxanyl, 1,4-benzodioxanyl, 1,2- or 1,3-dithiolanyl, 1,3-dithianyl, isoxazolyl, oxazolyl, morpholinyl, benzisoxazolyl, benzoxazolyl, isothiazolyl, thiazolyl, benzisothiazolyl, benzothiazolyl, benzothiazinyl, 1,2,4-, 1,2,5- or 1,3,4-oxadiazolyl, 1,2,3-, 1,2,4-, 1,2,5- or 1,3,4-thiadiazolyl, 1,2,3-, 1,2,5- or 1,3,4-triazolyl, 1,3,5-triazinyl, benzotriazolyl and 1,2,3,4-tetrazolyl, any of said groups in $R^3$, $R^4$ and $R^5$ being unsubstituted or substituted by $C_{1-4}$ alkyl, $C_{1-4}$ alkoxy, $C_{2-4}$ alkanoyl, $C_{2-4}$ alkanoyloxy, $C_{2-4}$ alkoxycarbonyl, halogen, nitro, cyano, trifluoromethyl, di-$C_{1-4}$ alkylamino, $C_{1-4}$ alkylthio, methylsulfinyl, methylsulfonyl, oxo, thioxo or $C_{1-4}$ alkanoylamido, and said cycloalkyl, cycloalkenyl, phenyl, naphthyl, indolyl, imidazolyl and heterocyclic groups when representing $R^3$, $R^4$ and $R^5$ being attached directly or through $C_{1-4}$ alkylene, to the carbon between -CO- and N of acylaminoacyl in the case of $R^3$, to the nitrogen in acylaminoacyl in the case of $R^4$, and to the carbonyl of the amido group in acylaminoalcyl in the case of $R^5$.

2. A compound according to claim 1, wherein R is acyl of the formula:

$$-COR^2$$

wherein $R^2$ is H or a member of the class consisting of $C_{1-18}$ alkyl, $C_{2-10}$ alkenyl, $C_{3-10}$ cycloalkyl, $C_{3-10}$ cycloalkenyl, phenyl, naphthyl or a heterocyclic group of the class consisting of azetidinyl, pyridyl, 1,2,3,4-tetrahydropyridyl, piperidyl, quinolyl, 1,2-dihydroquinolyl, 3- or 4-isoquinolyl, 1,2-dihydroisoquinolyl, pyrrolyl, pyrrolinyl, pyrrolidinyl, iodolyl, furyl, pyranyl, dihydropyranyl, benzofuryl, benzopyranyl, thienyl, benzothienyl, imidazolyl, pyrazolyl, pyrazinyl, pyrimidyl, pyridazinyl, 2-imidazolinyl, imidazolidinyl, benzimidazolyl, indazolyl, quinoxalyl, quinazolinyl, cinnolinyl, 1,4-dioxanyl, 1,4-benzodioxanyl, 1,2- or 1,3-dithiolanyl, 1,3-dithianyl, isoxazolyl, oxazolyl, morpholinyl, benzisoxazolyl, benzoxazolyl, isothiazolyl, thiazolyl, benzisothiazolyl, benzothiazolyl, benzothiazinyl, 1,2,4-, 1,2,5- or 1,3,4-oxadiazolyl, 1,2,3-, 1,2,4-, 1,2,5- or 1,3,4-thiadiazolyl, 1,2,3-, 1,2,5- or 1,3,4-triazolyl, 1,3,5-triazinyl, benzotriazolyl and 1,2,3,4-tetrazolyl, any of said $R^2$ groups being unsubstituted or substituted by $C_{1-4}$ alkyl, $C_{1-4}$ alkoxy, $C_{2-4}$ alkanoyl, $C_{2-4}$ alkanoyloxy, $C_{2-4}$ alkoxycarbonyl, halogen, nitro, cyano, trifluoromethyl, di-$C_{1-4}$ alkylamino, $C_{1-4}$ alkylamino, $C_{1-4}$ alkylthio, methlsulfinyl, methylsulfonyl, oxo, thioxo or $C_{1-4}$ alkanoylamido, and said cycloalkyl, cycloalkenyl, phenyl, naphthyl and heterocyclic groups being attached, directly or through a $C_{1-4}$ alkylene group, to the carbonyl group in the acyl radical R.

3. A compound according to claim 1, wherein R is acylaminoacyl of the formula:

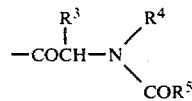

wherein $R^3$ is H, $C_{1-18}$ alkyl, $C_{3-10}$ cycloalkyl, phenyl, naphthyl, indolyl or imidazolyl, $R^4$ is H, $C_{1-18}$ alkyl, $C_{3-10}$ cycloalkyl, phenyl or naphthyl, and $R^5$ is H, $C_{1-18}$ alkyl, $C_{2-10}$ alkenyl, $C_{3-10}$ cycloalkyl, phenyl, naphthyl or a heterocyclic group of the class consisting of azetidinyl, pyridyl, 1,2,3,4-tetrahydropyridyl, piperidyl, quinolyl, 1,2-dihydroquinolyl, 3- or 4-isoquinolyl, 1,2-dihydroisoquinolyl, pyrrolyl, pyrrolinyl, pyrrolidinyl, indolyl, furyl, pyranyl, dihydropyranyl, benzofuryl, benzopyranyl, thienyl, benzothienyl, imidazolyl, pyrazolyl, pyrazinyl, pyrimidyl, pyridazinyl, 2-imidazolinyl, imidazolidinyl, benzimidazolyl, indazolyl, quinoxalyl, quinazolinyl, cinnolinyl, 1,4-dioxanyl, 1,4-benzodioxanyl, 1,2- or 1,3-dithiolanyl, 1,3-dithianyl, isoxazolyl, oxazolyl, morpholinyl, benzisoxazolyl, benzoxazolyl, isothiazolyl, thiazolyl, benzisothiazolyl, benzothiazolyl, benzothiazinyl, 1,2,4-, 1,2,5- or 1,3,4-oxadiazolyl, 1,2,3-, 1,2,4-, 1,2,5- or 1,3,4-thiadiazolyl, 1,2,3-, 1,2,5- or 1,3,4-triazolyl, 1,3,5-triazinyl, benzotriazolyl and 1,2,3,4-tetrazolyl, any of said groups in $R^3$, $R^4$ and $R^5$ being unsubstituted or substituted by $C_{1-4}$ alkyl, $C_{1-4}$ alkoxy, $C_{2-4}$ alkanoyl, $C_{2-4}$ alkanoyloxy, $C_{2-4}$ alkoxycarbonyl, halogen, nitro, cyano, trifluoromethyl, di-$C_{1-4}$ alkylamino, $C_{1-4}$ alkylthio, methylsulfinyl, methylsulfonyl, oxo, thioxo or $C_{1-4}$ alkanoylamido, and said cycloalkyl, cycloalkenyl, phenyl, naphthyl, indolyl, imidazolyl and heterocyclic groups representing $R^3$, $R^4$ and $R^5$ being attached directly or through $C_{1-4}$ alkylene, to the carbon between -CO- and N of acylaminoacyl in the case of $R^3$, to the nitrogen in acylaminoacyl in the case of $R^4$ and to the carbonyl or the amido group in acylaminoacyl in the case of $R^4$.

4. A compound according to claim 2, wherein $R^2$ is $C_{1-6}$ alkyl, $C_{3-7}$ cycloalkyl, phenyl or pyridyl, said alkyl, being unsubstituted or substituted by halogen, and said cycloalkyl, phenyl and pyridyl being attached, directly or through $C_{1-4}$ alkylene, to the carbonyl group in the acyl R.

5. A compound according to claim 3, wherein $R^3$, $R^4$ and $R^5$ are $C_{1-6}$ alkyl.

6. The compound according to claim 1, which is dechloromaytansinol.

7. The compound according to claim 1, which is dechloromaytansine.

8. The compound according to claim 1, which is D-dechloromaytansine.

9. The compound according to claim 1, which is dechloromaytansinol 3-isobutyrate.

10. The compound according to claim 1, which is dechloromaytansinol 3-nicotinate.

11. The compound to claim 1, which is dechloromaytansinol 3-cyclohexanecarboxylate.

12. The compound according to claim 1, which is dechloromaytansinol 3-phenylacetate.

13. The compound according to claim 1, which is dechloromaytansinol 3-chloroacetate.

14. A pharmaceutical composition suitable for inhibiting the growth of tumor cells and prolonging the survival time of a tumor-bearing warm blooded animal, which comprises as an active ingredient an effective amount of a compound of the formula:

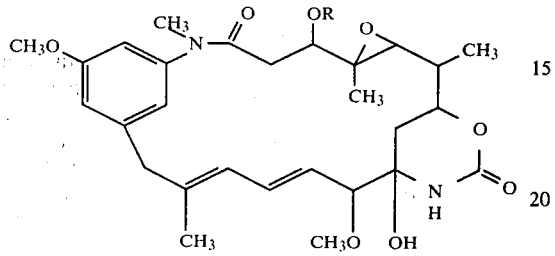

wherein R is H, acyl of the formula —COR$^2$ or acylamino of the formula

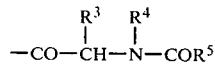

wherein R$^2$ is H or a member of the class consisting of C$_{1-18}$ alkyl, C$_{2-10}$ alkenyl, C$_{3-10}$ cycloalkyl, C$_{3-10}$ cycloalkenyl, phenyl, naphthyl or a group of the class consisting of azetidinyl, pyridyl, 1,2,3,4-tetrahydropyridyl, piperidyl, quinolyl, 1,2-dihydroquinolyl, 3-or 4-isoquinolyl, 1,2-dihydroisoquinolyl, pyrrolyl, pyrrolinyl, pyrrolidinyl, indolyl, furyl, pyranyl, dihydropyranyl, benzofuryl, benzopyranyl, thienyl, benzothienyl, imidazolyl, pyrazolyl, pyrazinyl, pyrimidyl, pyridazinyl, 2-imidazolinyl, imidazolidinyl, benzimidazolyl, indazolyl, quinoxalyl, quinazolinyl, cinnolinyl, 1,4-dioxanyl, 1,4-benzodioxanyl, 1,2- or 1,3-dithiolanyl, 1,3-dithianyl, isoxazolyl, oxazolyl, morpholinyl, benzisoxazolyl, benzoxazolyl, isothiazolyl, thiazolyl, benzisothiazolyl, benzothiazolyl, benzothiazinyl, 1,2,4-, 1,2,5- or 1,3,4-oxadiazolyl, 1,2,3-, 1,2,4-, 1,2,5- or 1,3,4-thiadiazolyl, 1,2,3-, 1,2,5- or 1,3,4-triazolyl, 1,3,5-triazinyl, benzotriazolyl and 1,2,3,4-tetrazolyl, any of said R$^2$ groups being unsubstituted or substituted by C$_{1-4}$ alkyl, C$_{1-4}$ alkoxy, C$_{2-4}$ alkanoyl, C$_{2-4}$ alkanoyloxy, C$_{2-4}$ alkoxycarbonyl, halogen, nitro, cyano, trifluoromethyl, di-C$_{1-4}$ alkylamino, C$_{1-4}$ alkylthio, methylsulfinyl, methylsulfonyl, oxo, thioxo or C$_{1-4}$ alkanoylamido, and said cycloalkyl, cycloalkenyl, phenyl, naphthyl and heterocyclic groups being attached directly or through a C$_{1-4}$ alkylene group to the carbonyl group in the acyl radical R; wherein R$^3$ is H, C$_{1-18}$ alkyl, C$_{3-10}$ cycloalkyl, phenyl, naphthyl, indolyl or imidazolyl, R$^4$ is H, C$_{1-18}$ alkyl, C$_{3-10}$ cycloalkyl, phenyl or naphthyl, and R$^5$ is H, C$_{1-18}$ alkyl, C$_{2-10}$ alkenyl, C$_{3-10}$ cycloalkyl, phenyl, naphthyl or a heterocyclic group of the class consisting of azetidiny, pyridyl, 1,2,3,4-tetrahydropyridyl, piperidyl, quinolyl, 1,2-dihydroquinolyl, 3- or 4-isoquinolyl, 1,2-dihydroisoquinolyl, pyrrolyl, pyrrolinyl, pyrrolidinyl, indolyl, furyl, pyranyl, dihydropyranyl, benzofuryl, benzopyranyl, thienyl, benzothienyl, imidazolyl, pyrazolyl, pyrazinyl, pyrimidyl, pyridazinyl, 2-imidazolinyl, imidazolidinyl, benzimidazolyl, indazolyl, quinoxalyl, quinazolinyl, cinnolinyl, 1,4-dioxanyl, 1,4-benzodioxanyl, 1,2- or 1,3-dithiolanyl, 1,3-dithianyl, isoxazolyl, oxazolyl, morpholinyl, benzisoxazolyl, benzoxazolyl, isothiazolyl, thiazolyl, benzisothiazolyl, benzothiazolyl, benzothiazinyl, 1,2,4-, 1,2,5- or 1,3,4-oxadiazolyl, 1,2,3-, 1,2,4-, 1,2,5- or 1,3,4-thiadiazolyl, 1,2,3-, 1,2,5- or 1,3,4-triazolyl, 1,3,5-triazinyl, benzotriazolyl and 1,2,3,4-tetrazolyl, any of said groups in R$^3$, R$^4$ and R$^5$ being unsubstituted or substituted by C$_{1-4}$ alkyl, C$_{1-4}$ alkoxy, C$_{2-4}$ alkanoyl, C$_{2-4}$ alkanoyloxy, C$_{2-4}$ alkoxycarbonyl, halogen, nitro, cyano, trifluoromethyl, di-C$_{1-4}$ alkylamino, C$_{1-4}$ alkylthio, methylsulfinyl, methylsulfonyl, oxo, thioxo or C$_{1-4}$ alkanoylamido, and said cycloalkyl, cycloalkenyl, phenyl, naphthyl, indolyl, imidazolyl and heterocyclic groups when representing R$^3$, R$^4$ and R$^5$ being attached directly or through C$_{1-4}$ alkylene, to the carbon between -CO- and N of acylaminoacyl in the case of R$^3$, to the nitrogen in acylaminoacyl in the case of R$^4$, and to the carbonyl of the amido group in acylaminoacyl in the case of R$^5$, and a pharmaceutically acceptable carrier or diluent therefor.

15. A method for inhibiting the growth of tumor cells and prolonging the survival time of a tumor-bearing warm blooded animal, which comprises administering to said animal an effective amount of a compound of the formula:

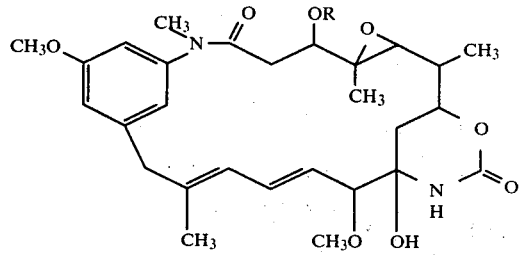

wherein R is H, acyl of the formula —COR$^2$ or acylaminoacyl of the formula

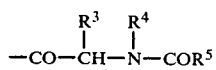

wherein R$^2$ is H or a member of the class consisting of C$_{1-18}$ alkyl, C$_{2-10}$ alkenyl, C$_{3-10}$ cycloalkyl, C$_{3-10}$ cycloalkenyl, phenyl, naphthyl or a group of the class consisting of azetidinyl, pyridyl, 1,2,3,4-tetrahydropyridyl, piperidyl, quinolyl, 1,2-dihydroquinolyl, 3- or 4-isoquinolyl, 1,2-dihydroisoquinolyl, pyrrolyl, pyrrolidinyl, pyrrolidinyl, indolyl, furyl, pyranyl, dihydropyranyl, benzofuryl, benzopyranyl, thienyl, benzothienyl, imidazolyl, pyrazolyl, pyrazinyl, pyrimidyl, pyridazinyl, 2-imidazolinyl, imidazolidinyl, benzimidazolyl, indazolyl, quinoxalyl, quinazolinyl, cinnolinyl, 1,4-dioxanyl, 1,4-benzodioxanyl, 1,2- or 1,3-dithiolanyl, 1,3-dithianyl, isoxazolyl, oxazolyl, morpholinyl, benzisoxazolyl, benzoxazolyl, isothiazolyl, thiazolyl, benzisothiazolyl, benzothiazolyl, benzothiazinyl, 1,2,4-, 1,2,5- or 1,3,4-oxadiazolyl, 1,2,3-, 1,2,4-, 1,2,5- or 1,3,4- thiadiazolyl, 1,2,3-, 1,2,5- or 1,3,4-triazolyl, 1,3,5-triazinyl, benzotriazolyl and 1,2,3,4-tetrazolyl, any of said $R^2$ groups being unsubstituted or substituted by $C_{1-4}$ alkyl, $C_{1-4}$ alkoxy, $C_{2-4}$ alkanoyl, $C_{2-4}$ alkanoyloxy, $C_{2-4}$ alkoxycarbonyl, halogen, nitro, cyano, trifluoromethyl, di-$C_{1-4}$ alkylamino, $C_{1-4}$ alkylthio, methylsulfinyl, methylsulfonyl, oxo, thioxo or $C_{1-4}$ alkanoylamido, and said cycloalkyl, cycloalkenyl, phenyl, naphthyl and heterocyclic groups being attached directly or through a $C_{1-4}$ alkylene group to the carbonyl group in the acyl radical R; wherein $R^3$ is H, $C_{1-18}$ alkyl, $C_{3-10}$ cycloalkyl, phenyl, naphthyl, indolyl or imidazolyl, $R^4$ is H, $C_{1-18}$ alkyl, $C_{3-10}$ cycloalkyl, phenyl or naphthyl, and $R^5$ is H, $C_{1-18}$ alkyl, $C_{2-10}$ alkenyl, $C_{3-10}$ cycloalkyl, phenyl, naphthyl or a heterocyclic group of the class consisting of azetidinyl, pyridyl, 1,2,3,4-tetrahydropyridyl, piperidyl, quinolyl, 1,2-dihydroquinolyl, 3- or 4-isoquinolyl, 1,2-dihyroisoquinolyl, pyrrolyl, pyrrolinyl, pyrrolidinyl, indolyl, furyl, pyranyl, dihydropyranyl, benzofuryl, benzopyranyl, thienyl, benzothienyl, imidazolyl, pyrazolyl, pyrazinyl, pyrimidyl, pyridazinyl, 2-imidazolinyl, imidazolidinyl, benzimidazolyl, indazolyl, quinoxalyl, quinazolinyl, cinnolinyl, 1,4-dioxanyl, 1,4-benzodioxanyl, 1,2- or 1,3-dithiolanyl, 1,3-dithianyl, isoxazolyl, oxazolyl, morpholinyl, benzisoxazolyl, benzoxazolyl, isothiazolyl, thiazolyl, benzisothiazolyl, benzothiazolyl, benzothiazinyl, 1,2,4-, 1,2,5- or 1,3,4-oxadiazolyl, 1,2,3-, 1,2,4-, 1,2,5- or 1,3,4-thiadiazolyl, 1,2,3-, 1,2,5- or 1,3,4-triazolyl, 1,3,5-triazinyl, benzotriazolyl and 1,2,3,4-tetrazolyl, any of said groups in $R^3$, $R^4$ and $R^5$ being unsubstituted or substituted by $C_{1-4}$ alkyl, $C_{1-4}$ alkoxy, $C_{2-4}$ alkanoyl, $C_{2-4}$ alkanoyloxy, $C_{2-4}$ alkoxycarbonyl, halogen, nitro, cyano, trifluoromethyl, di-$C_{1-4}$ alkylamino, $C_{1-4}$ alkylthio, methylsulfinyl, methylsulfonyl, oxo, thioxo or $C_{1-4}$ alkanoylamido, and said cycloalkyl, cycloalkenyl, phenyl, naphthyl, indolyl, imidazolyl and heterocyclic groups when representing $R^3$, $R^4$ and $R^5$ being attached directly or throuch $C_{1-4}$ alkylene, to the carbon between -CO- and N of acylaminoacyl in the case of $R^3$, to the nitrogen in acylaminoacyl in the case of $R^4$, and to the carbonyl of the amido group in acylaminoacyl in the case of $R^5$.

* * * * *